(12) United States Patent
Eriksson

(10) Patent No.: US 6,710,298 B2
(45) Date of Patent: Mar. 23, 2004

(54) DEVICE FOR METAL WELDING

(76) Inventor: Ingemar Eriksson, Parkvägen 10, S-780 44 Dala-Floda (SE)

( * ) Notice: Subject to any disclaimer, the term of this patent is extended or adjusted under 35 U.S.C. 154(b) by 0 days.

(21) Appl. No.: 10/203,507
(22) PCT Filed: Feb. 8, 2001
(86) PCT No.: PCT/SE01/00238
§ 371 (c)(1), (2), (4) Date: Aug. 8, 2002
(87) PCT Pub. No.: WO01/58400
PCT Pub. Date: Aug. 16, 2001

(65) Prior Publication Data
US 2003/0001950 A1 Jan. 2, 2003

(30) Foreign Application Priority Data
Feb. 11, 2000 (SE) .............................. 0000432

(51) Int. Cl.$^7$ ............................................. B23K 9/095
(52) U.S. Cl. .................................. 219/130.01; 219/147
(58) Field of Search ...................... 219/130.01, 147; 2/8

(56) References Cited

U.S. PATENT DOCUMENTS

| | | | | |
|---|---|---|---|---|
| 4,471,207 A | * | 9/1984 | Hawkes | 219/130.01 |
| 4,555,614 A | * | 11/1985 | Morris et al. | 219/130.01 |
| 4,698,484 A | * | 10/1987 | Babcock et al. | 219/130.01 |
| 6,230,327 B1 | * | 5/2001 | Briand et al. | 2/8 |
| 6,242,711 B1 | * | 6/2001 | Cooper | 219/130.01 |

FOREIGN PATENT DOCUMENTS

| FR | 2742287 | * | 6/1997 |
|---|---|---|---|
| GB | 2283103 | * | 4/1995 |

* cited by examiner

*Primary Examiner*—Clifford C. Shaw
(74) *Attorney, Agent, or Firm*—Rolf Fasth; Fasth Law Offices

(57) ABSTRACT

The invention relates to a device for metal welding, comprising a shielding element (1) which allows visual monitoring of the working process but protects the eyes from light radiation. The device comprises a video camera (5) which is directable towards the welding zone for recording the welding process in the form of video signals transmitted, via an image processing unit, to a video display unit (7), which the user is able to view and which is placed in or on the inside of the shielding element (1). The image processing unit reads process data from the video signals and presents the same via the video display unit.

5 Claims, 2 Drawing Sheets

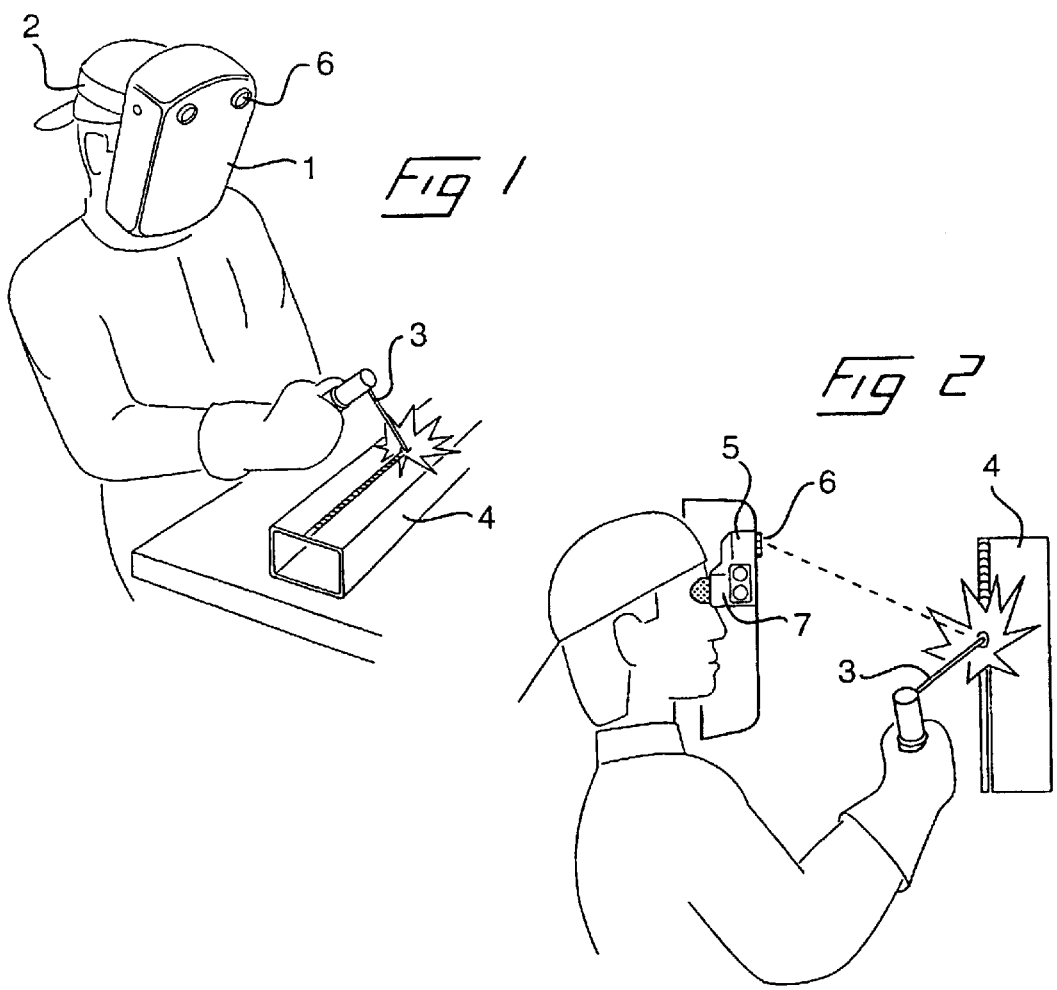
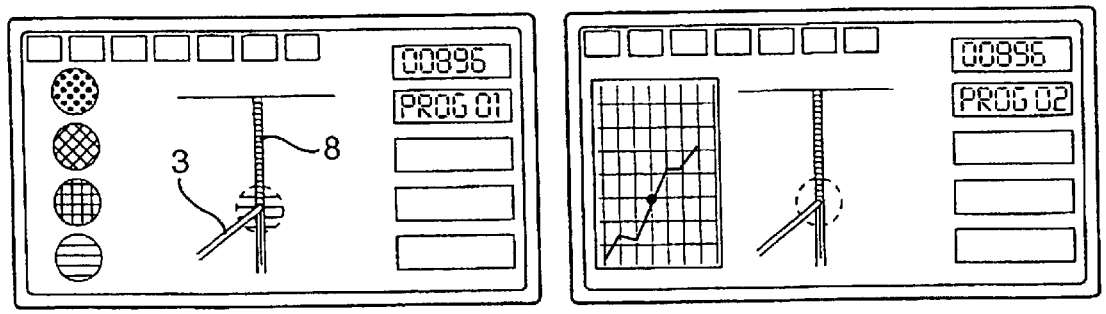

DEVICE FOR METAL WELDING

PRIOR APPLICATIONS

This application is a U.S. national phase application based upon International Application No. PCT/5E01/00238, filed Feb. 8, 2001; which claims priority from Swedish Application No. 0000432-5, filed Feb. 11, 2000.

The present invention relates to a device for metal welding, comprising a shielding element which allows visual monitoring of the working process but protects the eyes from light radiation.

BACKGROUND OF THE INVENTION

In metal welding, very powerful radiation is emitted, on the one hand, in the form of light radiation in the visible spectrum and, on the other, in the form of ultraviolet as well as infrared radiation. Such radiation is extremely injurious to the eyes and an operator must protect his eyes carefully when performing such work.

When designing eye-protecting devices for welding, the light radiation cannot be completely excluded since the operator must be able to visually monitor the working process.

The most common eye-protecting device in welding is the type that comprises a dark glass or filter glass which is arranged in spectacles, a shield, a mask, a visor or the like and during welding the filter glass is placed as a protection before the eyes. Such a filter glass is substantially non-transparent in case of normal light intensity and only the very intense light that arises when welding can pass through.

Another common type of eye-protecting device comprises a glass controlled by photocells which is composed of liquid crystals and which becomes dark and automatically dampens the light that passes through the glass when the welding starts. Under normal light conditions before and after welding, the glass is approximately as transparent as ordinary sunglasses.

Manual welding is a difficult and demanding task and long experience and training is required to master all types of welding of different materials and material thicknesses with different quality standards. Among other things, the welding temperature must be adjusted to the material and thickness in question, i.e. sufficiently high to obtain satisfactory fusing together of the materials but not so high as to make the material melt thoroughly and cause the forming of holes in the material.

Between these two extremes, the welding can be performed with a varying degree of quality, each material and material thickness having an optimum temperature at which the welding can be effected with optimum quality. Also the distribution of the temperature in the surrounding material is crucial to the quality of the completed weld.

The welding temperature depends on a number of factors and not only on the ambient temperature, the type of material and the material thickness, i.e. factors that are decisive of how fast the heat is led away from the actual welding zone, but also such factors as the thickness and the rate of motion of the welding rod, the material of the rod, the dimensions of the weld and, of course, the current intensity (in electric welding) or the nature of the flame (in gas welding).

Thus, a number of factors are decisive for the performance quality of the welding, and even with long experience it is difficult to control and consider all factors in order to achieve an optimum result.

Using prior-art welding equipment, the operator can get only little feedback on the operation which is being carried out and he has to trust the result that is visible to the eye. Moreover, the fact that the welder's eyes are protected by very dark filter glass and the build-up of smoke as well as the dazzling light that arises during welding render such visual control even more difficult.

Complete feedback on the performed work has been possible only in subsequent quality controls by careful visual inspection, impact testing using tools, x-ray testing, ultrasonic testing, tensile testing, pressure testing and the like. Besides the fact that most of these testing methods are time-consuming and require expensive equipment, the feedback actually arrives too late as the welding is already completed and consequently any deficiencies are difficult, time-consuming and expensive to rectify.

SUMMARY OF THE INVENTION

The present invention aims at obviating the disadvantages and deficiencies of prior-art devices and equipment for welding and providing a device by means of which a user gets immediate and continuous feedback on the performance of the welding by the presentation of process parameters that are important to the performance of the welding. At least these aims are achieved by means of a device according to claim 1.

The invention is thus based on the understanding that these aims can be achieved by means of a device comprising at least one video camera by means of which an image is recorded of the zone in which the welding is performed. The image is subsequently transmitted in the form of video signals to an image processing unit comprising some form of computer where the signals are analysed as to certain selected process parameters, such as the temperature, and processed to be presented to the user in a desired form via a video display unit in or on the inside of the shielding element. The process parameters can be used in a suitable manner and in a suitable form for preparation, monitoring, control and documentation of the welding process.

The preparation implies, for instance, that information about the workpiece such as type of material, dimensions, type of joint, etc, is entered into the device, and this data can subsequently be used in an optional manner for automatic control of the welding equipment or for providing recommended setting values to the operator.

A parameter that is particularly important to detect in welding is the temperature in the actual melting zone but also the heat distribution in the surrounding material. The temperature can be shown to the user in an arbitrary manner, for instance, by numerical data, diagrams or by colouring different temperature ranges differently which are shown in an image representing the weld and the surrounding zone. The image of the heat distribution can be further processed and compared with a pre-programmed ideal image of the material and dimension in question and could be used for automatic control of the welding process.

Other parameters which might be interesting to detect are, for instance, the distance, the moving rate of the welding rod or the form and character of the light reflection from different surfaces. The latter may require some kind of lamps or other sources of radiation which are directed towards the weld, and the degree of reflection may indicate, for instance, impurities or the filling ratio of molten welding material in a weld joint.

The invention is intended to be combinable with all existing types of shielding elements through which the user is able to follow the welding process visually. Thus, the invention can be combined with the above-mentioned dark filter glasses or with the glasses of liquid crystals which are controlled by photo cells in such manner that process data is presented to the user in an arbitrary form via a separate display. The display can suitably be integrated into the shielding element but could also be a separate unit designed, for instance, as spectacles carried by the user inside a conventional shielding element. The process data can suitably be presented in the outer areas of the visual field, for instance, with the aid of a "bar" or data strip in one of the border areas of the visual field, whereas the central parts of the visual field are kept free to allow visual monitoring of the welding process in conventional manner. The process data from the image processing can thus provide the user with important information about the welding process that helps him to perform the welding in such a manner as to reach a good final result. The display can also be of a transparent type and may in this case be placed in its entirety before one eye or alternatively both eyes and the user will still get a good overview of the welding process.

The scope of the invention also includes the possibility of combining the device with a type of shielding element which itself comprises a video display unit with the aid of which also the visual monitoring of the welding process is effected by means of a video camera. In this case, the same camera or cameras and the same video display unit can be used for visual monitoring as well as for presentation of process data by image analysis of the video signal in an image processing unit.

The image processing unit can optionally work continuously by continuously analysing and detecting all the video signals from the camera, or intermittently by the video signals being analysed at a certain interval, for instance, an interval of 1–10 s. The advantage of the latter is that it requires considerably less data capacity.

As a rule, the device preferably comprises some type of shield or visor which covers the user's entire face, because some types of welding light contains ultraviolet radiation which can cause burn injuries to the skin like a sun tan. In one embodiment, the shielding element could be part of an overall helmet which is provided with a visor and in which the shielding element, video display unit, ear protectors and fresh-air supply are integrated. Other types of welding radiation can be much less harmful and in these cases a protection device including a video display unit and covering the eyes only may be sufficient.

The video display unit can be designed in many different ways. Since the near point of the adult eye, i.e. the nearest point on which the eyes can focus, is situated about 15–25 cm before the eyes, it can be inappropriate to place a display immediately before the eyes. Such a device would be relatively unwieldy as the display must be placed at a long distance from the eyes and the device would thus take up a great deal of space in the direction away from the face. Instead the representation of the working zone is preferably viewed through some form of magnifying prism or lens/lens system. The actual imaging can be effected in an arbitrary manner, for instance, on an LCD or by projection from small projectors onto a light-reflecting screen, and the user can view this image via the magnifying prism/lens system.

The device can optionally comprise one video camera or two video cameras to allow stereoscopy. By stereoscopy it is possible, for instance, to calculate distances such as length, width and depth and this information could in turn be used to calculate volume, for instance, to ensure that a weld joint is filled with a sufficient amount of welding material or to calculate the rate at which the welding rod is moved during welding. Distances could, however, also be detected by other means than by two cameras, for instance by ultrasound. Furthermore, the camera can be self-acting so that it is automatically directed towards the weld irrespective of how the user holds his head. The control can, for instance, be effected by detection of and centring on the welding flame.

A device according to the invention can be improved by other optional functions, if desired. Besides being in communication with the image processing unit and the video display unit, the video camera or cameras can, for instance, also be in communication with some kind of video storing unit, such as a videotape recorder or CD/DVD player, for documentation and storage of the performance of the welding. This transmission of the video signals to the video storing unit can be effected in arbitrary manner, such as via a cable or by wireless transmission. In such a video storing unit, it is also possible to store documentation of checks on welds, for instance, controls of leakage and cracking such as X-ray and ultrasonic testing.

The device is primarily intended to be physically carried by the user in the form of a helmet, a visor or some other gear. The image processing unit and the video storing unit, if present, can however be placed at a distance from the user. It would, however, also be feasible to attach the device to an adjustable arm at a workbench or the like.

An inventive device could in a further developed embodiment be provided with a number of additional functions. The control of the welding equipment could, for instance, be effected manually or automatically via the computer of the image processing unit. Manually with the aid of information from the presented process data by means of suitably placed control buttons or display pointers or by voice control. Automatically by the computer controlling the welding equipment so that the welding process will be effected within pre-programmed desired values of certain process parameters, for instance the temperature, and as a function of equally pre-programmed input values, for instance concerning the material and the dimensions. The operator could also get instructions about the performance of the welding via the image processing unit, for instance, to increase or decrease the rate of motion of the welding rod.

The device could also be combined with a gas sensor to enable the operator to receive a warning by the image processing unit in case of explosive or poisonous gas at the place where the welding is being performed.

An instructor could be connected via the image processing unit to be able to follow the result of the welding performed by a welder in training. In this case, he would be able to give advice and instructions, for instance, in the form of text messages via the video display unit or voice messages via a loudspeaker/headset.

BRIEF DESCRIPTION OF THE ACCOMPANYING DRAWINGS

In the drawings

FIG. 1 is a perspective view of a person who is welding and is equipped with a device according to a first embodiment of the present invention;

FIG. 2 is a side view of the person with the device according to FIG. 1 partly in cross-section;

FIG. 3 is an example of a video image which the user can see during welding;

FIG. 4 is a second example of a video image which the user could see;

DETAILED DESCRIPTION OF PREFERRED EMBODIMENTS OF THE INVENTION

Figure 5:
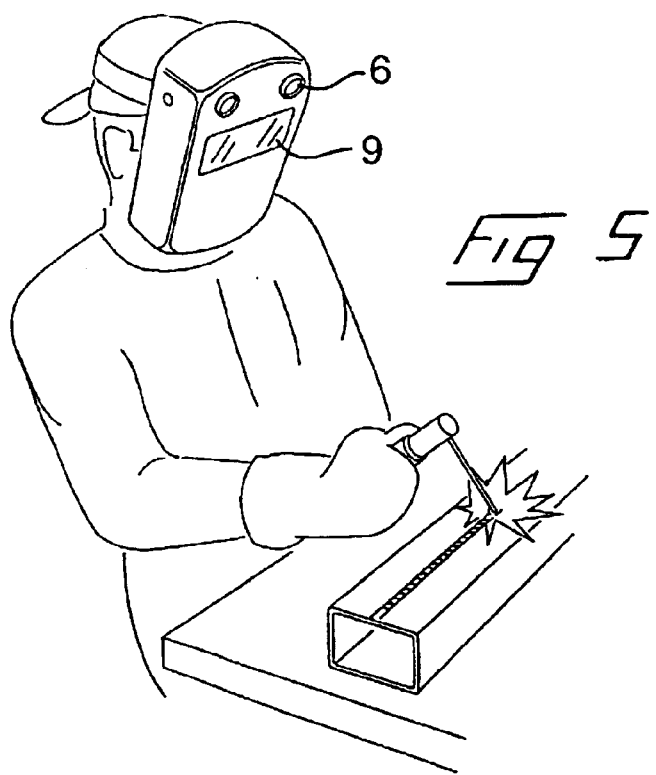
FIG. 5 is a perspective view of a person who is welding and is equipped with a device according to a second embodiment of the present invention.

Examples of feasible embodiments of the invention will now be described with reference to the accompanying drawings. FIGS. 1 and 2 illustrate a user who is welding and who has a device according to a first embodiment of the present invention. In this embodiment, the video cameras and the video display unit are used to show, by image processing, relevant information about the welding process to the user as well as to protect the user's eyes by letting him view the welding zone and the performance of the operation via the video display unit without needing a separate filter glass or the like. The device is designed as a visor or a shield 1, which covers the user's entire face and is retained in place by a cord 2 around the user's head. Reference numeral 3 designates a welding holder and a welding electrode which are used for welding on a workpiece 4.

The shown device comprises two video cameras 5 of which two lenses 6 are visible from the outside of the shield. In FIG. 2, the shield is shown partly in cross-section to illustrate in more detail the construction of the device. The light which is caught by the respective lenses 6 is converted in the video camera unit 5 into signals which are transmitted to a video display unit 7 to generate a video image which the user can see via a lens system (not shown in detail). The shown device comprises two video camera units and two video display units for generating a right-hand and a left-hand image, which can be viewed by the user's respective eyes, thus resulting in a stereo image with the possibility of visual depth.

FIGS. 3 and 4 illustrate various conceivable images which can be viewed by means of the device as the video camera is connected to an image processing unit (not shown). The latter can be carried by the user and be in communication with the video cameras and the video display unit via cables. However, the image processing unit can also be completely separate from the user and the communication can be effected wirelessly, also over great distances, for instance, to a monitoring station where information is collected from several working places. In the centre of the image, the actual working zone is shown with the welding electrode 3 and the weld joint 8 which is being made. On each side of the actual working zone, different types of information are illustrated which can be retrieved from the video recording by suitable image processing. FIG. 3 is intended to show the variation in temperature in the weld joint and the surrounding material by areas with different temperatures being coloured differently. The temperature value of the respective colours can suitably be indicated in the video image, as suggested, by different screen patterns to the left in FIG. 3. In case of too high or too low a welding temperature, the operator can easily change the settings of the welding assembly. Such a change of the settings of the welding assembly could also be performed by remote control via the video equipment, for instance, by means of control buttons on the video equipment or by voice control effected by the operator. The image processing is not limited to the measurement of temperature but many other functions can be integrated into the system and presented to the user in various optional views. FIG. 4 illustrates such an alternative view in which a chart, instead of colours, is shown for some important parameter, for instance, the variation in time of the temperature or welding voltage.

The image processing equipment, which preferably comprises a microprocessor, can be built into the actual video unit so that the entire equipment is carried by the user in a shield, helmet or the like. However, as previously mentioned, the video unit can be connected to an isolated unit, wirelessly or via a cable, which contains, for instance, an image processing and video storing unit. With the aid of equipment of the latter type, it is also possible for an instructor to follow a pupil's welding operation during training and/or welding certification and give him instructions as the work proceeds, for instance, in the form of text messages on the video screen or voice messages via a loudspeaker/headset.

Figure 6:
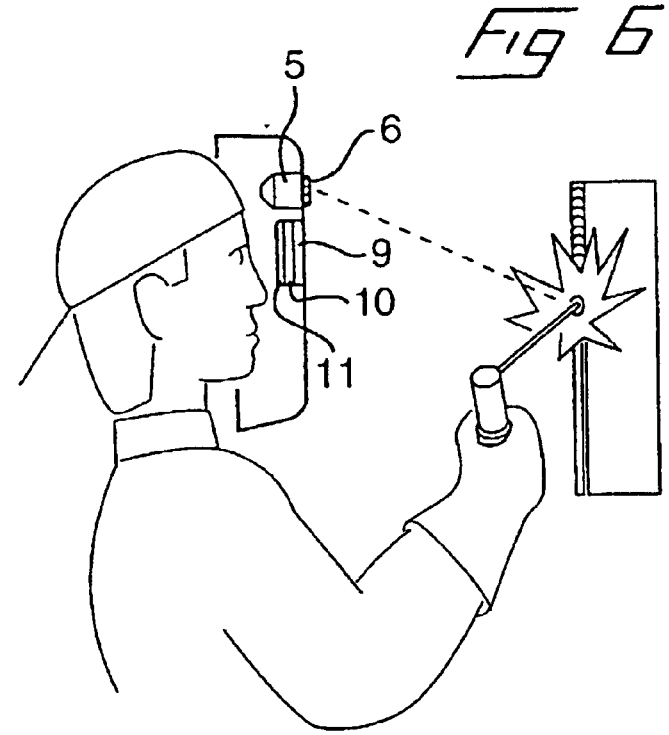
FIG. 6 is a side view of the person with the device according to FIG. 5 partly in cross-section.

FIGS. 5 and 6 show an alternative embodiment of the invention which, in addition to the video cameras 5, comprises a filter glass 9 made of dark glass or liquid crystals, through which the user can view the welding zone and the performance of the welding in a conventional manner. In this embodiment, the video display unit 7 has another design than in the embodiment according to FIGS. 1 and 2. On the inside of the filter glass 9, a display 10 is arranged which is of a flat and transparent type. By this arrangement, the user can view the welding zone through the filter glass 9 and the display 10. At the same time, it is possible to enter information about the welding process in the form of tables, diagrams, etc, preferably in the outer areas of the visual field. This is effected as described above by a video recording of the welding process by the cameras 5, an analysis of the welding process being performed in an image processing unit (not shown) and shown on the display 10. In order to eliminate the disadvantages caused by the short distance between the user's eyes and the display 10, a thin and flat lens 11 or a prism is arranged before the display to give the impression that the generated image is placed at a considerably longer distance from the eyes than it actually is.

In the described second embodiment of the invention, the information about the welding process is preferably presented in the outer areas of the visual field while the centre area is left to allow a good overview of the performance of the welding. Also in this case, it would, however, be possible, for instance, to colour areas with different temperatures differently as an additional aid in welding. This would be perfectly possible if the camera/display is adjusted to the eyes/filter glass so that the image generated on the display coincides with the view that the user can see directly through the filter glass.

What is claimed is:

1. A device for metal welding, comprising a shielding element (1) which allows visual monitoring of the working process but protects the eyes from light radiation, the shielding element being mountable on a user's head and having a video camera (5) disposed therein, the shielding element having a lens (6) mounted therein and the shielding element being free from any transparent glass at an eye-level of the user, the video camera being disposed in front and at the eye-level and being movable within the shielding element to be automatically directable towards a welding joint regardless of a direction of the head for recording the working process in the form of video signals transmitted, via an image processing unit, to a video display unit (7), which the user is able to view and which is placed in or on the inside of the shielding element (1) at the eye-level of the user, the image processing unit reading process data from the video signal and presenting a display of the same via the video display unit, the display showing a welding zone, the display changing a color of the welding zone depending upon a temperature at the welding zone.

2. A device as claimed in claim 1, wherein process data from the image processing unit as well as an image of the welding zone are viewable via the video display unit (7).

3. A device as claimed in claim 1, wherein the video display unit is combined with a filter glass (9) in such manner that the welding zone is viewable via the filter glass at the same time as process data is presented to the user via the video display unit (10).

4. A device as claimed in claim 3, wherein the video display unit (10) is transparent and placed before the filter glass (9).

5. A device as claimed in claim 1, wherein the video camera (5) is in communication with a video recording unit.

* * * * *